US008236369B2

(12) United States Patent
Chen

(10) Patent No.: US 8,236,369 B2
(45) Date of Patent: Aug. 7, 2012

(54) STENT COATING METHOD

(75) Inventor: Yung Ming Chen, Cupertino, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 12/840,178

(22) Filed: Jul. 20, 2010

(65) Prior Publication Data

US 2010/0285203 A1 Nov. 11, 2010

Related U.S. Application Data

(62) Division of application No. 11/442,005, filed on May 26, 2006, now Pat. No. 7,775,178.

(51) Int. Cl.
*A61L 33/00* (2006.01)

(52) U.S. Cl. ....... 427/2.24; 427/2.25; 427/457; 427/600

(58) Field of Classification Search .................... 347/10; 427/2.24

See application file for complete search history.

(56) References Cited

U.S. PATENT DOCUMENTS 4,697,195 A * 9/1987 Quate et al. .................... 347/46
5,722,479 A 3/1998 Oeftering
5,898,446 A 4/1999 Moriyama
6,217,151 B1 4/2001 Young
6,395,326 B1 * 5/2002 Castro et al. ................ 427/2.24
6,596,239 B2 7/2003 Williams et al.
6,645,547 B1 11/2003 Shekalim et al.
6,676,987 B2 * 1/2004 Zhong et al. ................ 427/2.24
6,867,248 B1 3/2005 Martin et al.
6,916,379 B2 7/2005 Shekalim et al.
6,971,813 B2 12/2005 Shekalim et al.
7,048,962 B2 5/2006 Shekalim et al.
7,208,190 B2 4/2007 Verlee
7,214,759 B2 5/2007 Pacetti et al.
7,323,210 B2 1/2008 Castro et al.
7,342,670 B2 3/2008 Teichman
7,344,599 B2 3/2008 Shekalim et al.
7,416,609 B1 8/2008 Madriaga et al.
7,455,876 B2 11/2008 Castro et al.
7,599,727 B2 10/2009 Teichman
2002/0126166 A1 * 9/2002 Ellson ............................ 347/10
2004/0053381 A1 3/2004 Williams et al.
2004/0068316 A1 4/2004 Schaeffer
2004/0076747 A1 4/2004 Shekalim et al.

(Continued)

FOREIGN PATENT DOCUMENTS

EP 0 586 187 3/1994

(Continued)

OTHER PUBLICATIONS

U.S. Appl. No. 11/305,662, filed Dec. 16, 2005, Sciver et al.

(Continued)

*Primary Examiner* — Dah-Wei Yuan
*Assistant Examiner* — Andrew Bowman
(74) *Attorney, Agent, or Firm* — Squire Sanders (US) LLP

(57) ABSTRACT

An apparatus and method for coating abluminal surface of a stent is described. A method for coating a stent can include stent mounting, stent movement, and droplet excitation. A method can include applying a coating to a stent, the applying including generating waves in a coating solution to eject droplets of the coating solution from a surface of the coating solution toward the stent, the generating performed by transducers submerged in the coating solution.

27 Claims, 7 Drawing Sheets

U.S. PATENT DOCUMENTS

| | | | |
|---|---|---|---|
| 2004/0117007 | A1 | 6/2004 | Whitbourne et al. |
| 2004/0185081 | A1 | 9/2004 | Verlee et al. |
| 2004/0202773 | A1 * | 10/2004 | Verlee et al. .................. 427/2.1 |
| 2004/0254634 | A1 | 12/2004 | Verlee et al. |
| 2005/0048194 | A1 | 3/2005 | Shmulewitz |
| 2005/0058768 | A1 | 3/2005 | Teichman |
| 2005/0241577 | A1 | 11/2005 | Shekalim et al. |
| 2006/0073265 | A1 | 4/2006 | Teichman et al. |
| 2006/0136048 | A1 | 6/2006 | Pacetti et al. |
| 2006/0156976 | A1 | 7/2006 | Shekalim et al. |
| 2006/0172060 | A1 | 8/2006 | Teichman et al. |
| 2006/0217801 | A1 | 9/2006 | Rosenthal |
| 2006/0233942 | A1 | 10/2006 | Shekalim |
| 2008/0003349 | A1 | 1/2008 | Van Sciver et al. |
| 2008/0206442 | A1 | 8/2008 | Shekalim et al. |
| 2008/0220174 | A1 | 9/2008 | Teichman |
| 2008/0226812 | A1 | 9/2008 | Chen |
| 2009/0232964 | A1 | 9/2009 | Chen |

FOREIGN PATENT DOCUMENTS

| | | |
|---|---|---|
| EP | 0 728 584 | 8/1996 |
| EP | 1 364 628 | 11/2003 |
| WO | WO 2004/012784 | 2/2004 |

OTHER PUBLICATIONS

International Search Report for PCT/US2006/015541, filed Apr. 18, 2006, mailed Jun. 29, 2007, 18 pgs.

Pouton et al., "Biosynthetic polyhydroxyalkanoates and their potential in drug delivery", Advanced Drug Delivery Reviews 18, pp. 133-162 (1996).

International Search Report for PCT/US2007/009113 filed Apr. 13, 2007, mailed Sep. 28, 2007, 15 pgs.

Elrod et al., "Nozzleless droplet formation with focused acoustic beams", J. of Applied Physics 65, No. 9, pp. 3441-3447 (1989).

* cited by examiner

Figure 3-Schematic diagram of a transducer assembly (50)

STENT COATING METHOD

CROSS-REFERENCE TO RELATED APPLICATIONS

This application is a divisional of application Ser. No. 11/442,005, filed May 26, 2006, now U.S. Pat. No. 7,775,178 which is incorporated herein by reference.

FIELD OF THE INVENTION

The present invention relates a method for coating a stent. More particularly, this invention provides a method to generate uniform and controllable droplets that can be used to rapidly coat the abluminal surface (selective areas or entire outside surface) of a stent.

BACKGROUND

Percutaneous transluminal coronary angioplasty (PTCA) has revolutionized the treatment of coronary arterial disease. A PTCA procedure involves the insertion of a catheter into a coronary artery to position an angioplasty balloon at the site of a stenotic lesion that is at least partially blocking the coronary artery. The balloon is then inflated to compress against the stenosis and to widen the lumen to allow an efficient flow of blood through the coronary artery. However, restenosis at the site of angioplasty continues to hamper the long term success of PTCA, with the result that a significant proportion of patients have to undergo repeated revascularization.

Stenting has been shown to significantly reduce the incidence of restenosis to about 20 to 30%. On the other hand, the era of stenting has brought a new problem of in-stent restenosis. As shown in FIG. 1, a stent 2 is a scaffolding device for the blood vessel and it typically has a cylindrical configuration and includes a number of interconnected struts 4. The stent is delivered to the stenosed lesion through a balloon catheter. Stent is expanded to against the vessel walls by inflating the balloon and the expanded stent can hold the vessel open.

Stent can be used as a platform for delivering pharmaceutical agents locally. The inherent advantage of local delivery the drug over systematic administration lies in the ability to precisely deliver a much lower dose of the drug to the target area thus achieving high tissue concentration while minimizing the risk of systemic toxicity.

Given the dramatic reduction in restenosis observed in these major clinical trials, it has triggered the rapid and widespread adoption of drug-eluting stents (DES) in many countries. A DES consisting of three key components, as follows: (1) a stent with catheter based deployment device, (2) a carrier that permits eluting of the drug into the blood vessel wall at the required concentration and kinetic profile, and (3) a pharmaceutical agent that can mitigate the in-stent restenosis. Most current DES systems utilize current-generation commercial stents and balloon catheter delivery systems.

The current understanding of the mechanism of restenosis suggests that the primary contributor to re-narrowing is the proliferation and migration of the smooth muscle cells from the injured artery wall into the lumen of the stent. Therefore, potential drug candidates may include agents that inhibit cell proliferation and migration, as well as drugs that inhibit inflammation. Utilizing the synergistic benefits of combination therapy (drug combination) has started the next wave of DES technology.

Strict pharmacologic and mechanical requirements must be fulfilled in designing the drug-eluting stents (DES) to guarantee drug release in a predictable and controlled fashion over a time period. In addition, a high speed coating apparatus that can precisely deliver a controllable amount of pharmaceutical agents onto the selective areas of the abluminal surface of a stent is extremely important to the DES manufactures.

There are several conventional coating methods have been used to apply the drug onto a stent, e.g. by dipping the stent in a coating solution containing a drug or by spraying the drug solution onto the stent. Dipping or spraying usually results in a complete coverage of all stent surfaces, i.e., both luminal and abluminal surfaces. The luminal side coating on a coated stent can have negative impacts to the stent's deliverability as well as the coating integrity. Moreover, the drug on the inner surface of the stent typically provides for an insignificant therapeutic effect and it get washed away by the blood flow. While the coating on the abluminal surface of the stent provides for the delivery of the drug directly to the diseased tissues.

The coating in the lumen side may increase the friction coefficient of the stent's surface, making withdrawal of a deflated balloon more difficult. Depending on the coating material, the coating may adhere to the balloon as well. Thus, the coating may be damaged during the balloon inflation/deflation cycle, or during the withdrawal of the balloon, resulting in a thrombogenic stent surface or embolic debris.

Defect formation on the stents is another shortcoming caused by the dipping and spraying methods. For example, these methods cause webbing, pooling, or clump between adjacent stent struts of the stent, making it difficult to control the amount of drug coated on the stent. In addition, fixturing (e.g. a mandrel) used to hold the stent in the spraying method may also induce coating defects. For example, upon the separation of the coated stent from the mandrel, it may leave some excessive coating material attached to the stent, or create some uncoated areas at the interface between the stent struts and mandrel. The coating weight and drop size uniformity control is another challenge of using aforementioned methods.

Another coating method involves the use of inkjet or bubble-jet technology. The drop ejection is generated by the physical vibration through an piezoelectric actuation or by thermal actuation. In an example, single inkjet or bubble jet nozzle head can be devised as an apparatus to precisely deliver a controlled volume coating substance to the entire or selected struts over a stent, thus it mitigates some of the shortcomings associated with the dipping and spraying methods. Typically, this operation involves moving an ejector head along the struts of a stent to be coated, but its coating speed is inherently much slower than, for example, an array coating system which consists of many transducers and each transducer can generate droplets to coat a stent simultaneously. This coating apparatus enables to generate droplets at single or multiple locations simultaneously on demand, thus it allows to coat stent in a much faster and versatile way (e.g. line printing rather than dot printing).

Furthermore, nozzle clogging, which may adversely affect coating quality, is a common problem to spraying, inkjet, and bubble-jet methods. Cleaning the nozzles results in a substantial downtime, decreased productivity, and increased maintenance cost.

It has been shown that focused and high intensity sound beams can be used for ejecting droplets. It is based on a constructive interference of acoustic waves—the acoustic waves will add in-phase at the focal point. Droplet formation using a focused acoustic beam is capable of ejecting liquid drop as small as a few microns in diameter with good reliability. It typically requires an acoustic lens to focus the acoustic waves.

The present invention provides a stent coating apparatus and method that overcome the aforementioned shortcomings from the conventional coating methods. The stent coating apparatus of the present invention can coat the abluminal surface of a stent at a high speed, and it can deliver a precise amount of coating material to the specific stent surfaces. Furthermore, the present invention does not use a nozzle, thus it eliminates the potential nozzle clogging issues.

According to the present invention, the stent coating apparatus includes a stent support, a coating device, and an imaging system. The stent support provides the mechanisms to hold a stent in place on a mandrel and to control the rotational and circumferential movement of the stent during the coating.

The coating apparatus includes a reservoir, a transducer assembly, and an ejection logic controller. The reservoir is used to hold a coating solution; a transducer assembly is used to generate acoustic energy to actuate the drop ejection from the surface of the coating solution; the ejection logic provides a control can over the position of droplet ejection. Transducers can be differentially turned on or off to steer the excitation of the droplets, and the droplet formation can be controlled only at the areas of the stent that need be coated. The advantage of this technique is it provides a reliable ejection of the fluids "on demand" without clogging the ejection aperture because the area of each ejection focal point is a relatively small region to the aperture.

The transducer assembly includes a plurality of transducers, RF drive device, and an ejection controller. Each transducer (e.g. piezoelectric transducer) can convert electrical energy into waves, such as ultrasonic waves. The transducer assembly generates acoustic waves and they propagate in the solution toward the liquid/air interface. Those waves are constructively interfered at a focal point of the solution surface, i.e., the waves will add in-phase at the focal point. The focused energy causes a droplet to be ejected from the surface of the coating solution. The wave frequency or amplitude can be used to adjust the droplet volume or droplet velocity.

In an embodiment of the invention, the constructively interfered waves are generated in certain patterns by controlling only portion of the transducers from the transducer arrays. Preferably, a switching system (or an ejection logic control) is linked to an imaging system to energize the transducers according to the stent strut position.

In an embodiment of the invention, the controller commands the transducer arrays to simultaneously eject droplets at multiple ejection points on the surface of the coating solution so that the stent can be coated simultaneously.

In an embodiment of the invention, the stent is preferably positioned above the ejector to receive the droplets generated from the surface of coating solution. In another embodiment, stent can be placed beneath the ejector. It will be appreciated by one of the ordinary skill in the art that embodiments of the invention enable to position the stent or the ejector in any orientation.

In an embodiment of the invention, the stent coating apparatus includes at least one assisted device, an imaging device. The image system is to track the stent strut location, to control the stent movement, and to communicate the information to the ejection logic controller. Accordingly, an imaging device with a feedback control is used to communicate to the stent holder controller to orient the stent to a particular position to receive the droplets generated by the corresponding coating device.

SUMMARY

Briefly and in general terms, the present invention is directed to a method of coating a surface of a stent. In aspects of the invention, a method comprises applying a coating to a stent. The applying includes generating waves in a coating solution to eject droplets of the coating solution from a surface of the coating solution toward the stent. The generating is performed by transducers submerged in the coating solution. In detailed aspects, the generated waves are in-phase with each other at an ejection point at which a droplet is ejected from the surface of the coating solution.

In other aspects of the present invention, a method comprises powering a plurality of transducers to produce acoustic waves in a coating solution that eject droplets from the coating solution toward a stent, and using an image of the stent to align a strut of the stent and one of the ejected droplets with each other. In detailed aspects, the transducers are submerged in the coating solution. In other aspects, the acoustic waves are in-phase with each other.

The features and advantages of the invention will be more readily understood from the following detailed description which should be read in conjunction with the accompanying drawings.

DETAILED DESCRIPTION OF PREFERRED EMBODIMENTS

Figure 1:
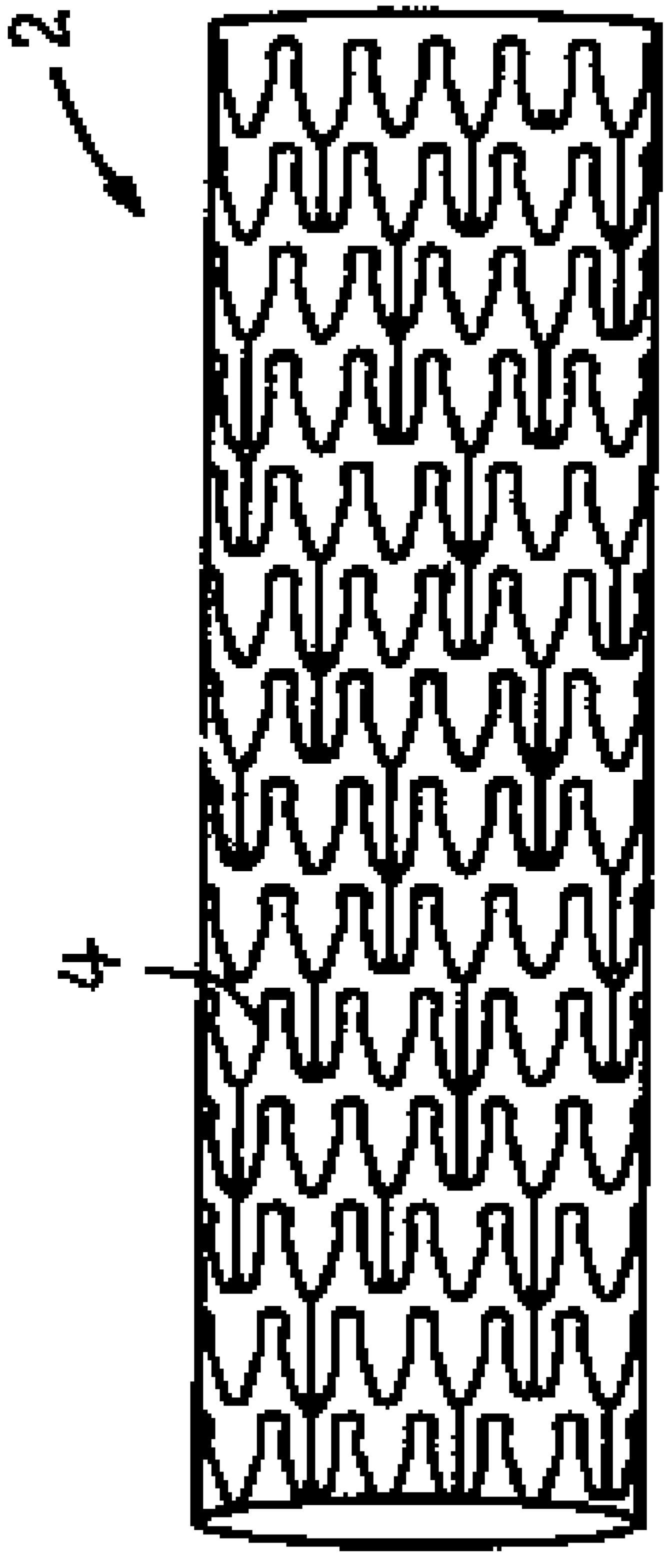
FIG. 1 Prior Art
FIG. 1 is a drawing to show a typical stent design.
Figure 2:
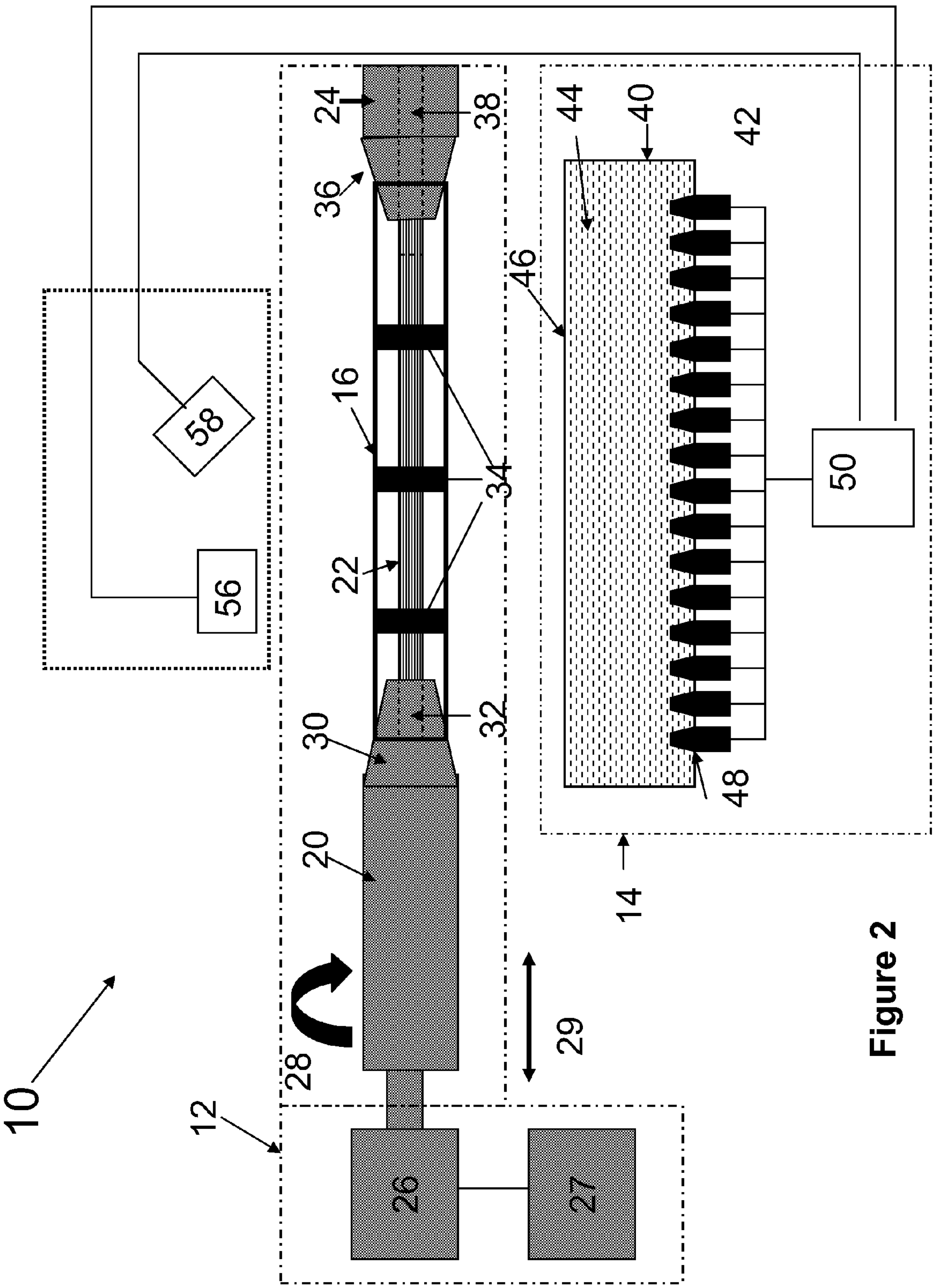
FIG. 2 is a schematic view of a stent coating apparatus according to an embodiment of the present invention.

FIG. 2 illustrates a stent coating apparatus 10. The apparatus 10 includes a stent handling 12, a coating device 14, and an imaging system, 56 and 58. The stent handling system 12 is to provide the supports to a stent 16 which is connected to motor 26 and motor 27 so as to control stent's circumferential and translational movements. The coating device 14 applies a coating to the stent 16.

In the embodiment shown in FIG. 2, the stent support 12 includes a shaft 20, a mandrel 22, and an optional lock member 24. The lock member 24 is optional if the mandrel 22 by itself can support the stent 16. The support member 20 is connected to a motor 26 to rotate the stent in the circumferential direction, so as motor 27 to translate the stent in the longitudinal direction of the stent 16, as depicted by the arrows 28 and 29.

In this embodiment, the support member 20 includes a conical end portion 30 and a bore 32 for receiving a first end of the mandrel 22. The first end can be threaded to screw into the bore 32 or can be retained within the bore 32 by a friction fit. The bore 32 should be deep enough to allow the mandrel 22 to mate securely with the support member 20. The depth of the bore 32 can also be further extended to allow a significant length of the mandrel 22 to penetrate or screw into the bore 32. The bore 32 can also extend completely through the support member 20. This would allow the length of the mandrel 22 to be adjusted to accommodate stents of various sizes. The mandrel 22 may also include a plurality of ridges 34 that add rigidity to and support to the stent 16 during coating. The ridges 34 may have a diameter of slightly less than the inner diameter of the stent 16. While three ridges 34 are shown, it will be appreciated by one of ordinary skill in the art that additional, fewer, or no ridges may be present, and the ridges may be evenly or unevenly spaced.

The lock member 24 also may include a conical end portion 36. A second end of the mandrel 22 can be permanently affixed to the lock member 24 if the first end is disengageable from the support member 20. Alternatively, the mandrel 22 can have a threaded second end for screwing into a bore 38 of the lock member 24. The bore 38 can be of any suitable depth that would provide the lock member 24 incremental movement with respect to the support member 20. The bore 38 on the lock member 24 can also be made as a through hole. Accordingly, stents of any length can be secured between the support member 20 and the lock members 20 and 24. In accordance with this embodiment, the second end lock member 24 contains a through hole 38 enabling the second end lock member to slide over the mandrel 22 to keep the stent 16 on the mandrel 22.

The coating device 14 shown in FIG. 2 includes a reservoir 40 and a transducer assembly 42. The reservoir 40 is used to hold a coating substance 44 to be applied to the stent 16. The transducer assembly 42 is submerged in the reservoir 40. The transducer assembly 42 generates acoustic energy to eject droplets from the surface 46 of the coating solution 44 to coat the stent 16. Preferably, the locations of the ejection points on the surface 46 of the coating substance 44 are matched to the stent strut areas that need to be coated.

The reservoir 40 may have any suitable configuration and may be disposed at any suitable location. For example, the reservoir 40 may have a cylindrical, elliptical or parallelepiped configuration. Preferably, the reservoir 40 encompasses the entire stent 16 so that droplets ejected from the surface 46 can reach all areas of the stent 16. Alternatively, the reservoir 40 may cover only an area of the stent to be coated. In a preferred embodiment, the reservoir 40 is positioned directly underneath the stent. Also, a short distance between the stent and the surface of reservoir 46 is maintained to ensure a stable droplet ejection.

Figure 3:
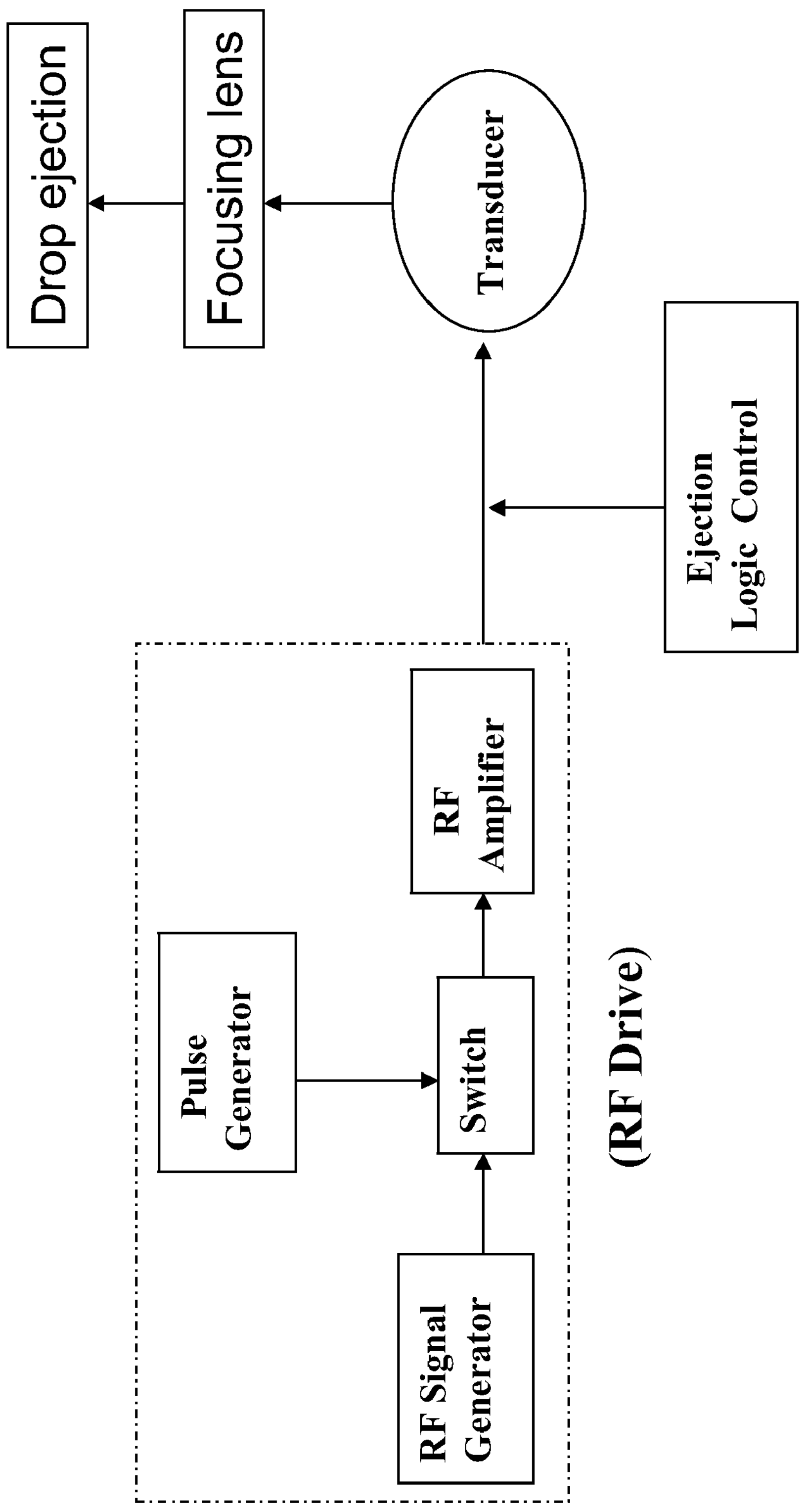
FIG. 3 is a schematic diagram of a transducer assembly.

As shown in FIG. 2, the transducer assembly 42 includes a plurality of transducers 48 and a controller 50 that is programmed to control the transducers 48. Each transducer 48 is used to generate the acoustic energy in the form of sound or ultrasound waves. Each transducer 48 preferably is a piezoelectric device, although it can be any other device suitable for generating ultrasound waves. The use of focused acoustic beam to eject droplets of controlled diameter and velocity from a free-liquid surface are well known in the art. FIG. 3 is a schematic diagram to show the mechanism of generating the droplet on demand using transducer arrays.

The controller 50 may be used to control the frequency, amplitude, and phase of the waves generated by each transducer 48 and to turn on or off the power supplied to the transducer 48. To generate a droplet at a predetermined point on the surface 46, the controller 50 controls the transducers 48 to generate waves that constructively interfere at this predetermined point. The focused acoustic energy causes a droplet to be ejected from the surface 46 of the coating substance 44 to coat the stent 16. Adjusting the frequency and amplitude of the ultrasound waves allows control over the ejection speed and volume of the droplet.

Figure 4:
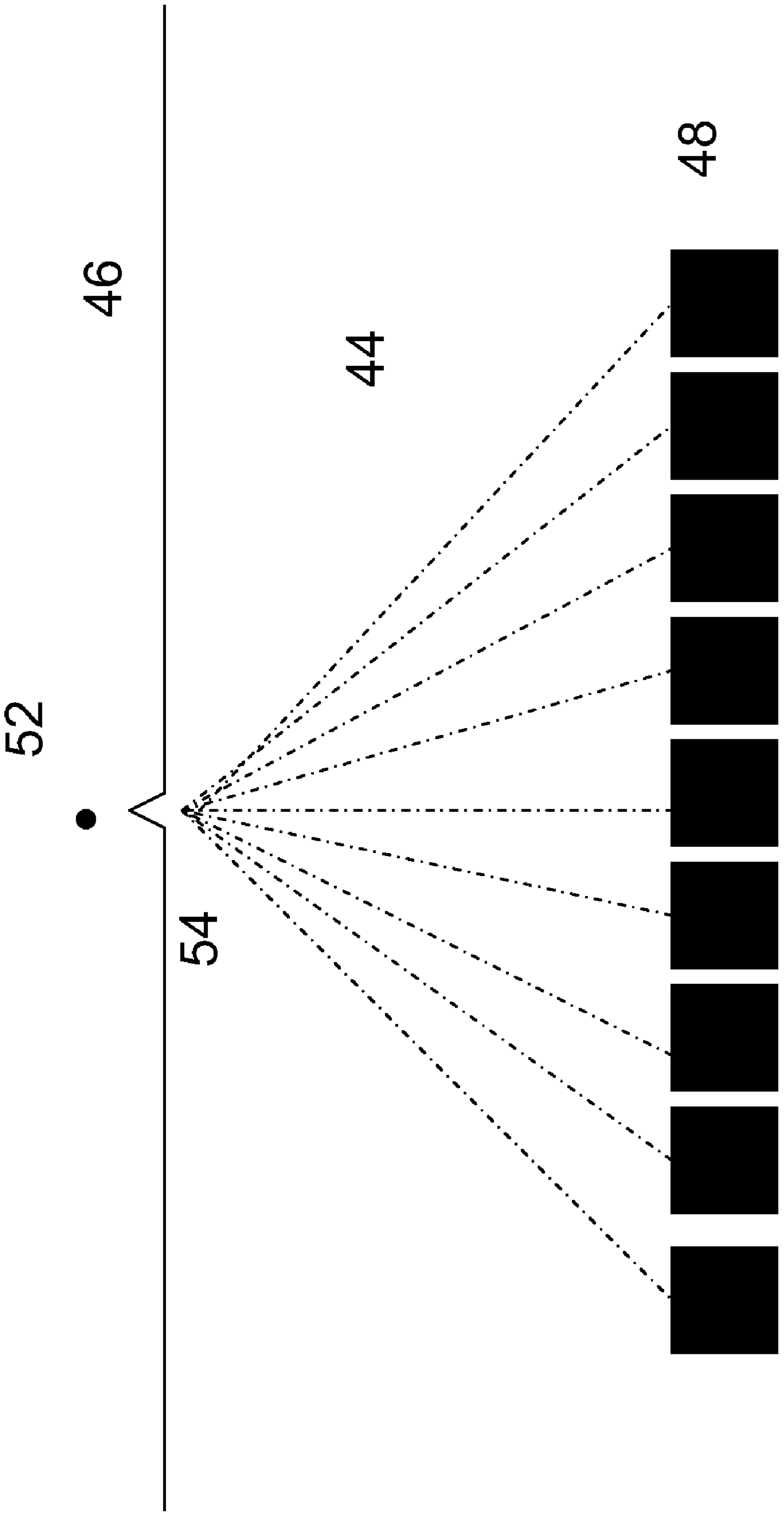
FIG. 4 is an example of generating single droplet using a transducer array according to an embodiment of the present invention.

FIG. 4 depicts the mechanism of generating a droplet from the surface of a coating substance. As illustrated in FIG. 4, a coating substance 44 is contained in a reservoir (not shown); also, there are nine transducers 48 submerged in the coating substance 44. The transducers 48 are used to generate focused in-phase waves at a predetermined ejection point 54 on the surface 46 of the coating substance 44. In other words, the waves are coherently constructed (in phase) at the ejection point (focal point) 54. The focused (through the acoustic lens) acoustic energy creates the required pressure at the ejection point 54, to eject a droplet 52 from the surface 46 onto the stent surface. In order for the waves to arrive at the ejection point 54 in phase, the transducers 48 should generate the waves at different times. In the example shown in FIG. 4, each of the first and ninth transducers, which are farthest from the ejection point 54, should first generate a wave. The fifth transducer, which is the closest to the ejection point 54, is the last to generate a wave. The precise timing for progressively generating the waves can be determined by a person of ordinary skill in the art and will not be discussed herein.

According to the present embodiment, as illustrated in FIG. 2, stent 16 is coated line by line as the stent rotates. The droplet ejection is controlled in a linear fashion and the droplet is generated only in the section that stent strut is detected. Preferably, these ejection points are aligned to stent's longitudinal direction, and the coating substance is received only on the stent's outside surfaces. The ejection points are determined through the image controllers to verify if a stent strut is present. Thus, the ejection can be excited accordingly. Excitation of drops can start from one end and ending at the other end, or the droplets can be fired in segment or in all.

The droplet formation can be generated by singe or combination of any number of transducers 48 in the reservoir 40. In some embodiments, the number of transducers used to generate each droplet may be seven. For example, the first droplet may be generated by transducers Nos. 1 to 7, the second droplet by Nos. 2 to 8, the third droplet by Nos. 3 to 9, . . . and so on. In some other embodiments, the number of transducers for generating a droplet may vary from droplet to droplet. For example, the first droplet may be generated by nine transducers, the second droplet by five, the third droplet by 15, . . . and so on. Preferably, the transducers used to generate a droplet are symmetrically arranged about the ejection point from which the droplet is ejected. Non-symmetrically arranged transducers tend to eject a droplet in a direction oblique to the surface of the coating substance. But one of ordinary skill in the art recognizes that an asymmetrical arrangement of the transducers can also be utilized to generate any specific ejection patterns by adjusting the timing, amplitude, or frequency of waves.

One preferred embodiment as shown in FIG. 2, the transducers 48 are arranged linearly and evenly spaced. In general, however, the transducer array can be arranged in any suitable manner. For example, instead of being arranged in a single row as shown in FIG. 2, the transducers may be arranged in two or multiple parallel rows. Additionally, the total required number of transducers 48 included in the transducer assembly 42 can vary depending on the application. For example, the number of transducers may range from 5 to 10,000, from 10 to 2,000, from 20 to 1,000, from 30 to 600, or from 40 to 400.

Figure 5:
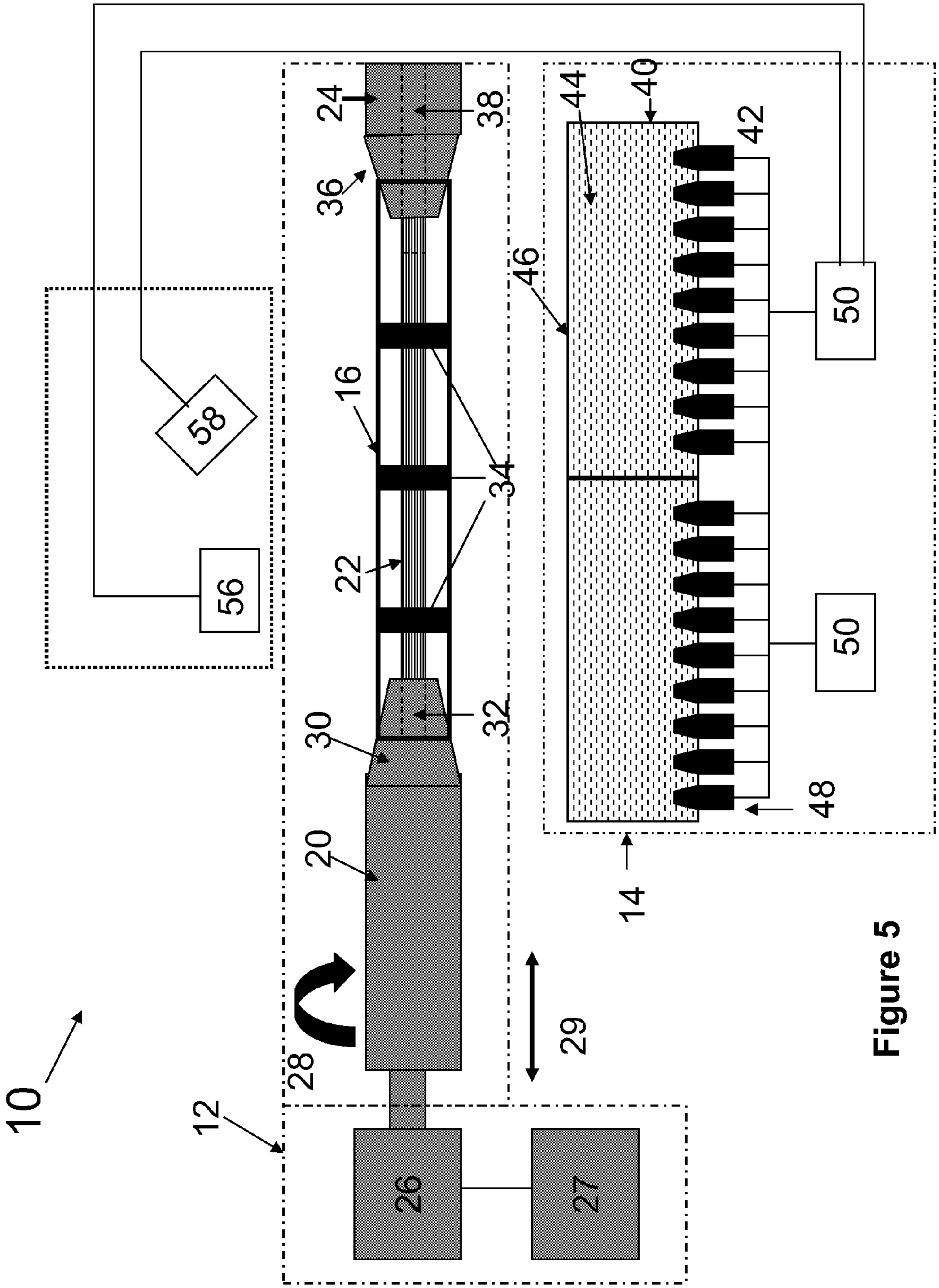
FIG. 5 is a schematic view of a stent coating apparatus includes more than one coating device.

The stent coating apparatus 10 shown in FIG. 2 is used to illustrate an example of using only one coating device 14 to coat the stent. This apparatus can be easily expanded to contain a dual-reservoir or multiple-reservoir coating system that will allow to accelerate the coating speed or it will allow to apply different formulations onto a stent. For example, as shown in FIG. 5, a stent coating apparatus 110 includes two coating assemblies 114a and 114b that are laterally arranged next to each other. Each assembly may contain different therapeutic agent. The therapeutic agent can be applied over the stent in sequence (i.e. layer by layer) to achieve a synergist effect. For example, the first coating assembly 114a is used to apply a layer of drug A over the stent 16, while the second assembly 114b is used to apply another layer of drug B on top of drug A layer.

As illustrated in FIG. 2, the stent coating apparatus 10 may include a first vision device 56 that images the stent 16 before or after the coating substance 44 has been applied to the stent 16. The first imaging device 56, along with a second imaging device 58 located a distance from the stent 16, are both communicatively coupled to the controller 50 of the transducer assembly 42. Based on the image provided by the imaging devices 56, 58, the controller 50 actuates the ejection of the droplets to coat only selected areas of the stent 16 accordingly.

After a section of the stent 16 has been coated, the coating device 14 may be stopped from dispensing the coating substance, and the imaging device 56 may begin to image the stent section to determine if the section has been adequately coated. This determination can be made by measuring the difference in color or reflectivity of the stent section before and after the coating process. If the stent section has been adequately coated, the stent coating apparatus 10 will begin to coat a new section of the stent 16. If the stent section is not coated adequately, then the stent coating apparatus 10 will recoat the stent section.

In an embodiment of the invention, the imaging devices 56, 58 can include charge coupled devices (CCDs) or complementary metal oxide semiconductor (CMOS) devices. In an embodiment of the invention, the imaging devices can be combined into a single imaging device. Further, it will be appreciated by one of ordinary skill in the art that placement of the imaging devices 56, 58 can vary as long as the devices have an acceptable view of the stent 16.

During the operation of the stent coating apparatus 10 illustrated in FIG. 2, the stent 16 is first mounted on the mandrel 22 of the stent support 12. The stent 16 is then rotated about its longitudinal axis by the motor 26 of the stent support 12. Once the stent 16 starts to rotate, the controller 50 of the coating device 14 commands the transducers 48 to generate in phase acoustic waves at one or more predetermined ejection points on the surface 46. Droplets are ejected at the focal points and get dispensed onto the stent 16. Additionally, the droplet volume can be tuned by adjusting the frequencies, and the drop velocity can be controlled by changing the wave amplitude. Furthermore, one or two imaging devices 56, 58 may be used to generate an image of the stent 16 to be used to direct the droplets to selected areas of the stent 16.

Figure 6:
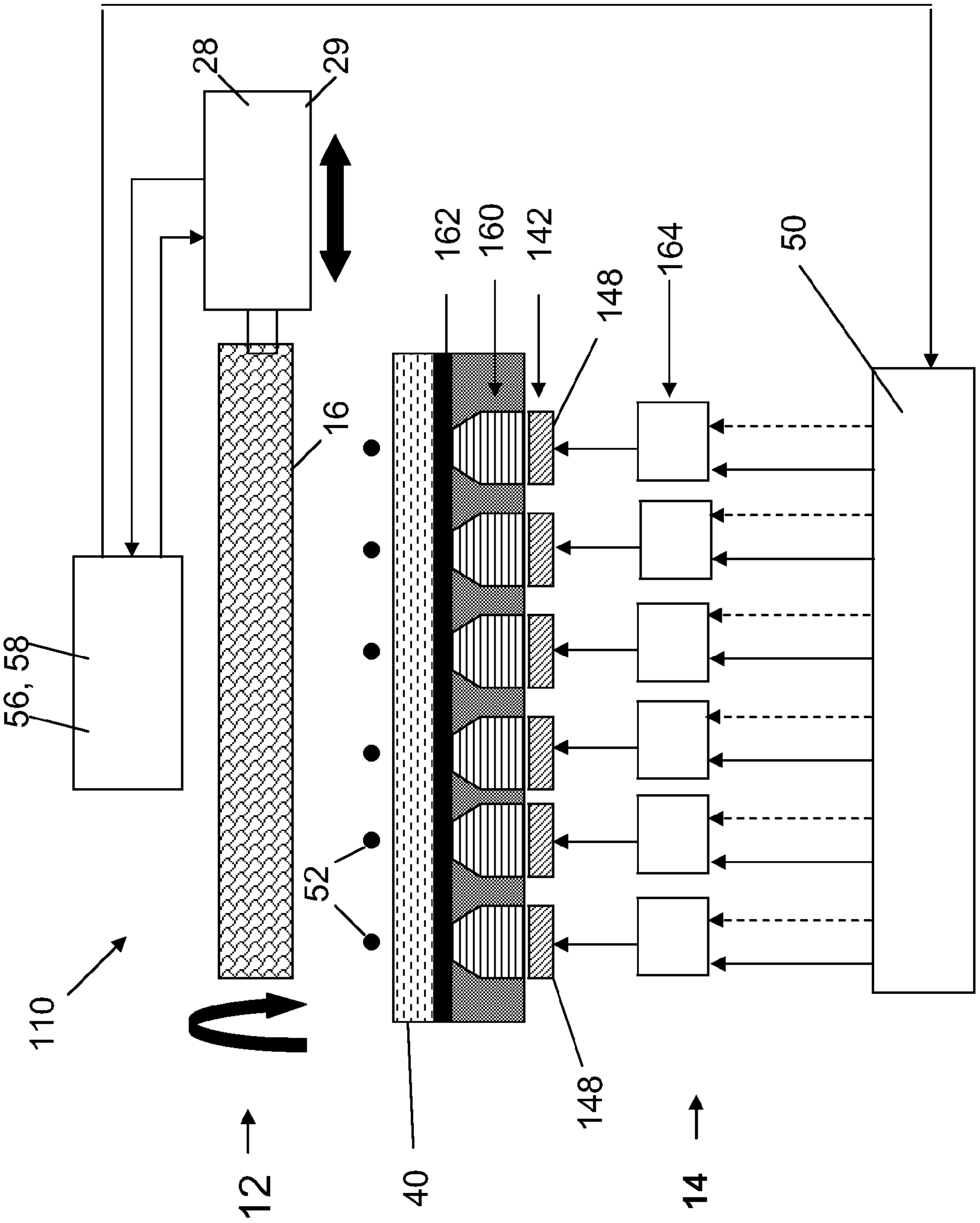
FIG. 6 is a schematic diagram of external transducer arrays containing a single reservoir.

Although the transducer assemblies 42 of the above-described embodiments are placed inside the reservoir 40 and submerged in a coating substance during operation, it is possible to place a transducer assembly outside of a reservoir. FIG. 6 illustrates a stent coating apparatus 110 that includes a reservoir 40 and a transducer assembly 142 that is placed outside of the reservoir 40. In some embodiments, it may be preferable to place only some, but not all, of the transducers of the transducer assembly outside of the reservoir. The stent coating apparatus 110 may further include an acoustic lens 160 placed preferably between each transducer 148 and the reservoir 40. Each acoustic lens 160 may have any suitable configuration, such as a concave configuration. The acoustic lenses 160 may be in direct contact with the coating substance or indirectly in contact with the coating substance through a coupling fluid 162 (external to the solution reservoir). The transducer assembly 142 may include (or may be coupled to) drive electronics, such as an ejection control 50, an RF amplifier, RF switches, and RF drives 164.

Figure 7:
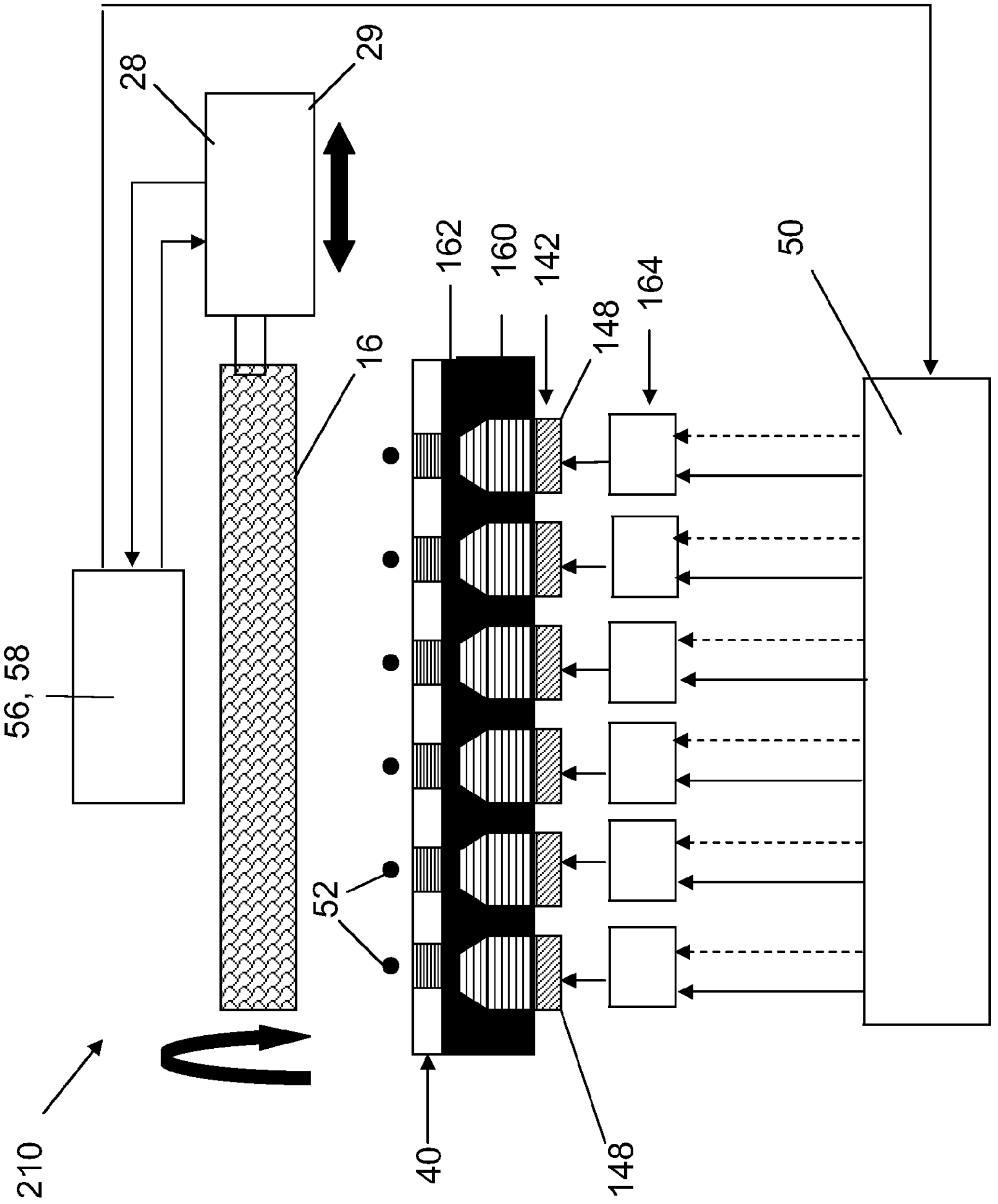
FIG. 7 is a schematic diagram of external transducer arrays containing multiple individual reservoirs.

Furthermore, although the embodiment shown in FIG. 6 has only one reservoir 40, one or more additional reservoirs may be added, and each reservoir may have one or more transducers. In the embodiment 210 shown in FIG. 7, for example, there is a reservoir 240 for each transducer 148.

The present invention offers many advantages over the prior art. For example, the present invention has the ability of coating stent abluminal surface only. A controlled volume of drops are generated and precisely delivered to the selective stent struts, thus it provides a better therapeutic control and it avoids the coating defects that are occurred in spraying and dipping methods. Additionally, the coating speed can be significantly increased through the transducer arrays design that enables coating the stent at multiple locations at a time. Furthermore, the present invention utilizes a nozzleless coating apparatus, thereby it eliminates the nozzle clogging issue which is a common issue to many conventional coating methods.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method for coating a stent, the method comprising:
applying a coating to a stent, the applying performed by a plurality of transducers, each transducer generating an acoustic wave in a coating solution, the acoustic wave being in-phase with another acoustic wave generated by another one of the transducers, the acoustic waves being in-phase with each other at an ejection point on a surface of the coating solution from which droplets of the coating solution are ejected.

2. The method of claim 1, further comprising imaging the stent to track movement of the stent.

3. The method of claim 2, further comprising determining, based on an image of the stent, a location for the ejection point from among a plurality of locations on the surface of the coating solution.

4. The method of claim 3, wherein the transducers are arranged symmetrically in a lateral direction with respect to the ejection point.

5. The method of claim 1, wherein the transducers cause droplets to form only at predetermined focal points on the surface of the coating solution.

6. The method of claim 1, wherein the applying includes ejecting a first droplet using a first plurality of the transducers and ejecting a second droplet using a second plurality of the transducers, the second droplet ejected independently of the first droplet.

7. The method of claim 6, wherein the first plurality of transducers is arranged laterally to the second plurality of transducers.

8. The method of claim 6, wherein the first droplet is of a first coating solution and the second droplet is of a second coating solution different in composition from the first coating solution.

9. The method of claim 1, wherein the applying includes adjusting excitation frequency of the transducers.

10. The method of claim 1, further comprising communicating a feedback image of the stent to a controller device that powers the transducers.

11. The method of claim 10, wherein the feedback image is used to align an ejected droplet and strut of the stent with each other.

12. The method of claim 1, wherein the droplets are ejected only on struts of the stent detected by an imaging device.

13. A method for coating a stent, the method comprising:

powering a plurality of transducers configured to produce acoustic waves in a coating solution that eject droplets from the coating solution toward a stent; and controlling timing at which the acoustic waves are produced by the transducers so that the acoustic waves are in-phase with each other at an ejection point at which the droplets are ejected from a surface of the coating solution.

14. The method of claim 13, wherein the transducers are submerged in the coating solution.

15. The method of claim 13, further comprising repositioning the stent based on a difference between images of a strut of the stent, the images taken before and after droplets of the coating solution are applied to the stent.

16. The method of claim 13, further comprising causing acoustic waves from the transducers to constructively interfere with each other at the ejection point.

17. A method for coating a stent, the method comprising:

powering a plurality of transducers configured to produce acoustic waves in a coating solution that eject droplets from the coating solution from a plurality of ejection points toward a stent;

determining, from among the plurality of ejection points on a surface of the coating solution, an ejection point at which the droplets are to be ejected from the surface of the coating solution, the determining of the ejection point based on an image of the stent; and controlling on/off timing for each of the transducers based at least partially on the distance of the individual transducer from the ejection point so that the acoustic waves arrive in-phase with each other at the ejection point.

18. A method for coating a stent, the method comprising:

powering a plurality of transducers configured to produce acoustic waves in a coating solution that eject droplets from the coating solution from a plurality of ejection points toward a stent;

determining, from among the plurality of ejection points on a surface of the coating solution, an ejection point at which the droplets are to be ejected from the surface of the coating solution, the determining of the ejection point based on an image of the stent; and causing each of the transducers to produce an acoustic wave timed in such a way that the produced acoustic waves constructively interfere at the ejection point and provide sufficient pressure to eject a droplet from the surface of the coating solution.

19. The method of claim 13, wherein the transducers are symmetrically arranged about the ejection point.

20. The method of claim 13, wherein the transducers are non-symmetrically arranged about the ejection point.

21. The method of claim 20, wherein the non-symmetrically arrange transducers cause a droplet to be ejected from the ejection point at an oblique direction from the surface of the coating solution.

22. The method of claim 17, wherein the transducers are symmetrically arranged about the ejection point.

23. The method of claim 17, wherein the transducers are non-symmetrically arranged about the ejection point.

24. The method of claim 23, wherein the non-symmetrically arrange transducers cause a droplet to be ejected from the ejection point at an oblique direction from the surface of the coating solution.

25. The method of claim 18, wherein the transducers are symmetrically arranged about the ejection point.

26. The method of claim 18, wherein the transducers are non-symmetrically arranged about the ejection point.

27. The method of claim 26, wherein the non-symmetrically arrange transducers cause a droplet to be ejected from the ejection point at an oblique direction from the surface of the coating solution.

* * * * *